US010209168B2

(12) United States Patent
Dudda et al.

(10) Patent No.: US 10,209,168 B2
(45) Date of Patent: Feb. 19, 2019

(54) MEASURING INSTRUMENT FOR THERMOGRAVIMETRICALLY DETERMINING THE MOISTURE CONTENT OF A MATERIAL

(71) Applicant: SARTORIUS LAB INSTRUMENTS GMBH & CO. KG, Goettingen (DE)

(72) Inventors: Olaf Dudda, Goettingen (DE); Wilfried Spannagel, Goettingen (DE); Daniel Faerger, Goettingen (DE)

(73) Assignee: SARTORIUS LAB INSTRUMENTS GMBH & CO. KG, Goettingen (DE)

( * ) Notice: Subject to any disclaimer, the term of this patent is extended or adjusted under 35 U.S.C. 154(b) by 82 days.

(21) Appl. No.: 15/277,237

(22) Filed: Sep. 27, 2016

(65) Prior Publication Data
US 2017/0016810 A1    Jan. 19, 2017

Related U.S. Application Data

(63) Continuation of application No. PCT/EP2015/000301, filed on Feb. 11, 2015.

(30) Foreign Application Priority Data

Mar. 27, 2014  (DE) ........................ 10 2014 104 279

(51) Int. Cl.
*G01N 5/04* (2006.01)
*G01G 1/00* (2006.01)
(Continued)

(52) U.S. Cl.
CPC .............. *G01N 5/045* (2013.01); *G01G 1/00* (2013.01); *G01G 17/04* (2013.01); *G01N 25/00* (2013.01); *G01N 25/56* (2013.01)

(58) Field of Classification Search
CPC .......... G01N 5/045; G01N 25/00; G01G 1/00; G01G 17/04
See application file for complete search history.

(56) References Cited

U.S. PATENT DOCUMENTS 6,092,924 A  *  7/2000  Scalese .................. G01N 22/04
                                                      333/208
8,046,176 B2 * 10/2011  Spannagel ............. G01G 17/04
                                                      702/24
(Continued)

FOREIGN PATENT DOCUMENTS

DE          10022099 A1    11/2001
EP           2574900 A1     4/2013

OTHER PUBLICATIONS

Office Action in corresponding German Application No. 102014104279.4, dated Nov. 17, 2014.
(Continued)

*Primary Examiner* — Lisa Caputo
*Assistant Examiner* — Philip Cotey
(74) *Attorney, Agent, or Firm* — Edell, Shapiro & Finnan, LLC

(57) ABSTRACT

A measuring instrument for thermogravimetrically determining the moisture content of a material, which includes a base (12), configured as a balance, with a base surface (22), and a hood (14) pivotably connected to the base. The hood has a weighing chamber lid (50), weighing chamber walls (52-56) and a heating element (44). The hood consists of an electronics module (36) that includes the heating element and an electronic power unit, and of a mechanical module (48) that includes the weighing chamber lid and all of the weighing chamber walls. The mechanical module (48) is rigidly and reversibly coupled to the electronics module so that the heating element, protrudes from a main body (42) of the electronics module and rises through a corresponding (Continued)

opening (58) in the rearward weighing chamber wall (56), with the main body being pivotably connected to the base and surrounding the electronic power unit.

14 Claims, 2 Drawing Sheets

(51) Int. Cl.
*G01N 25/00* (2006.01)
*G01G 17/04* (2006.01)
*G01N 25/56* (2006.01)

(56) References Cited

U.S. PATENT DOCUMENTS

| | | | | |
|---|---|---|---|---|
| 9,329,114 | B2* | 5/2016 | Dieffenbacher | G01N 5/045 |
| 9,360,405 | B2* | 6/2016 | Meister | G01N 5/025 |
| 2001/0039831 | A1* | 11/2001 | Olesen | G01N 5/02 |
| | | | | 73/73 |
| 2006/0027670 | A1* | 2/2006 | Shdaimah | G01N 5/025 |
| | | | | 236/44 C |
| 2006/0208098 | A1* | 9/2006 | Shdaimah | G01N 5/025 |
| | | | | 236/44 C |
| 2007/0245813 | A1* | 10/2007 | Luchinger | F26B 3/283 |
| | | | | 73/76 |
| 2007/0256479 | A1* | 11/2007 | Luchinger | G01N 5/045 |
| | | | | 73/76 |
| 2010/0086004 | A1* | 4/2010 | Dellar | F27B 5/04 |
| | | | | 374/14 |
| 2013/0081452 | A1* | 4/2013 | Meister | G01N 5/025 |
| | | | | 73/73 |
| 2013/0081453 | A1* | 4/2013 | Albrecht | G01N 5/045 |
| | | | | 73/73 |

OTHER PUBLICATIONS

International Search Report in counterpart International Application No. PCT/EP2015/000301, dated May 7, 2016.
International Preliminary Report on Patentability in counterpart International Application No. PCT/EP2015/000301, dated Mar. 29, 2016.
"Operating instructions moisture analyzer HB43-S", Dec. 2011, XP055183561, retrieved from the internet: http://us.mt.com/dam/product_organizations/laboratory_weighing/moisture/products/hb43_s/documentation/en/HB43-S_OI_en_11780961A.pdf.
"Instruction manual MB35 moisture analyzer", Jan. 2002, XP055183555, retrieved from the internet: http://www.scalenet.com/pdf/Ohaus_MB35_Moisture_Balance_Manual.pdf.

* cited by examiner

MEASURING INSTRUMENT FOR THERMOGRAVIMETRICALLY DETERMINING THE MOISTURE CONTENT OF A MATERIAL

CROSS REFERENCE TO RELATED APPLICATIONS

This is a Continuation of International Application PCT/EP2015/000301, which has an international filing date of Feb. 11, 2015, and the disclosure of which is incorporated in its entirety into the present Continuation by reference. The following disclosure is also based on and claims the benefit of and priority under 35 U.S.C. § 119(a) to German Patent Application No. DE 10 2014 104 279.4, filed Mar. 27, 2014, which is also incorporated in its entirety into the present Continuation by reference.

FIELD OF THE INVENTION

The invention relates to a measuring instrument for thermogravimetrically determining the moisture content of a material, said measuring instrument comprising
  a base, which is configured as a balance and which has a base surface, which forms at least one weighing chamber floor and through which a weighing pan support passes, and
  a hood, which is pivotably connected to the base and which has a weighing chamber lid and weighing chamber walls as well as at least one heating element, which has an effect on the chamber surrounded by the weighing chamber walls and which is in electrical contact with an electronic power unit.

BACKGROUND

Such measuring instruments, which will be interchangeably referred to herein as drying balances, are known from the European patent EP 2 574 900 A1.

Expressed in simple terms, a drying balance is a balance that is connected to a closed, heatable weighing chamber, in which the sample to be weighed can be positioned on a weighing pan, which is connected to a weighing device by way of a load receiver and can be heated by a heating device until the moisture contained in the sample to be weighed has at least partially escaped. The amount of weight that the sample to be weighed loses due to the moisture loss is recorded by the weighing device, so that the recorded weight profile can be used to draw conclusions about the moisture relevant properties of the sample to be weighed. The latter typically takes place in an electronic control unit, which is connected to the weighing device and which is also used to drive the electronic power unit, which supplies the heating element with the requisite operating voltage. The heating element itself can be implemented, for example, as a heating rod that radiates infrared radiation, as a microwave radiator or in any other way.

The aforementioned, generic publication discloses a base, which comprises an outer housing, in which both the weighing device as well as the control unit and the electronic power unit are included. The upper surface of the housing is configured in a stepped manner and forms both the weighing chamber floor as well as the rearward weighing chamber wall that faces away from the ordinary user. This rearward wall of the weighing chamber is horizontally traversed by a load arm, which functions as a weighing pan support and forms the mechanical connection between the weighing pan, disposed in the weighing chamber, and the weighing device, disposed inside the housing. Pivotally connected to the housing is a hood, which forms the two side walls and the front wall of the weighing chamber as well as a lid of the weighing chamber and contains the heating element below the lid of the weighing chamber. In the closed state of the hood the heating element makes contact with a contact point of the base, which is electrically connected to the electronic power unit in the interior of the housing. In order to open the hood, the hood can be pivoted into its open position, so that the weighing plan is accessible for loading with a sample to be weighed. The drawback with the known device is that the weighing chamber is difficult to clean. Especially in the case of drying balances not only pure water, but also other fluids, which can condense on the walls of the weighing chamber and can form deposits, which are difficult to remove, evaporate as a function of the specific sample to be weighed. This evaporation is not just a visual problem; rather there is the risk that subsequent loads of the sample to be weighed will be contaminated. The problem is made worse by the heating element, which is disposed in the hood and through which the deposits can be permanently burned into the material, of which the wall is made.

SUMMARY

One object of the present invention is to provide a drying balance that is easier to clean.

This object is achieved in conjunction with the features disclosed and claimed hereinafter. According to one aspect of the invention, the drying balance is provided with a hood that consists of two separate modules, i.e., an electronics module, comprising the heating element and the electronic power unit, and a mechanical module, comprising the weighing chamber lid and all of the weighing chamber walls. The mechanical module is rigidly and reversibly coupled to the electronics module in such a way that the heating element, which protrudes from a main body of the electronics module, extends through a corresponding opening in the rearward weighing chamber wall. The main body is pivotably connected to the base and surrounds the electronic power unit.

Preferred embodiments of the invention are the subject matter of various dependent claims.

First, the invention provides that the hood is made of several structural elements, the two modules, which can be either easily separated or assembled by the user. The two modules are divided primarily according to functional aspects. The entire electronics package that is required for the heating process, i.e., the heating element itself and the electronic power unit, which supplies the heating element with its operating voltage, is combined in the electronics module. In contrast, the purely mechanically acting components, i.e., all of the walls of the weighing chamber and the lid of the weighing chamber, are combined in the mechanical module. However, this approach is problematic in so far as it is necessary for an efficient heating of the sample to be weighed that the heating element, thus, a part of the electronics module, rises into the weighing chamber, i.e., into the chamber enclosed by the mechanical module. This problem is solved according to the invention by the feature that the electronics module, which typically must also have, as explained in greater detail below, electrical connections to the base, is pivotally hinged to the base, in particular, to its rearwards region and has a compact main body, in which the electronic power unit is housed. From this main body the actual heating element is directed towards the front. The rearward weighing chamber wall, which is a part of the mechanical module, has a corresponding opening, through which the heating element extends. The coupling between the mechanical module and the electronics module is reversible, so that the entire mechanical module can be removed from or mounted again on the electronics module, where in this case the heating element has to be run through the corresponding opening in the rearward wall of the weighing chamber.

Then the hood-like mechanical module is easily accessible for cleaning. In particular, the mechanical module can be easily packed into a washing machine, since it does not contain any electronic components. When the mechanical module is removed, the heating element, which itself can also be the object of contamination, juts, freely accessible, out from the main body of the electronic module and is also easily accessible for cleaning.

Heating elements, which are designed as infrared radiant heaters, in particular, heating elements that are made of a ceramic material, are quite susceptible to shock due to the brittle material properties of the ceramic. Therefore, when coupling or decoupling the mechanical module, one should try to avoid bumping against the heating element with the lid of the weighing chamber or with a wall of the weighing chamber. On the other hand, the opening in the rearward weighing chamber wall, through which the heating element extends into the weighing chamber, should be as small as possible. In order to resolve, among other things, this conflict of goals, it is provided in a further development of the invention that in parallel to the heating element, at least one guide rail sticks out of the main body of the electronics module, and onto this guide rail the mechanical module is pushed reversibly with corresponding guide elements. When the mechanical module is removed, the user does not have to exercise any particular caution, since the degrees of freedom of motion of the mechanical module are limited by the guide rail and the corresponding guide elements in such a way that only a precisely defined retraction movement is possible. More specifically, this retraction movement should be configured in such a way that contact between the heating element and the walls of the weighing chamber or with the lid of the weighing chamber is reliably prevented. In contrast, when mounting the mechanical module, the user has only to make sure that the guide rail and the corresponding guide elements find each other; and during the finding phase bumping against the heating element should be avoided. However, as soon as the guide rail and the guide elements have found each other, the degrees of freedom of motion of the mounting movement are again restricted in such a way that there can be no question about contact between the heating element and the wall of the weighing chamber or the lid of the weighing chamber.

Often the weighing pan of a drying balance is surrounded by a ring-shaped draft shield, which is supposed to prevent any air turbulence inside the hood from adversely affecting the measurement during the weighing process. Usually the draft shield is securely attached to the floor of the weighing chamber. However, this is inconvenient during the loading process. In contrast, it is provided in an advantageous embodiment of the invention that, furthermore, the mechanical module has a ring-shaped draft shield, which is arranged in the chamber that is surrounded by the walls of the weighing chamber and which in the closed state of the hood totally surrounds the weighing pan support. In other words, in this embodiment the draft shield is fixed between the walls of the weighing chamber and is an essential part of the mechanical module.

It is convenient if the main body of the electronics module comprises a coupling detector, with which the respective current state of coupling between the electronics module and the mechanical module is detectable. For example, the coupling detector can be designed as a micro-switch that is pressed when the rearward wall of the weighing chamber is pressed against the main body of the electronics module. The coupling detector may be connected to the electronic control unit, which is implemented as a safety measure, so that the electronic power unit can supply the heating element with operating voltage, only if the mechanical module and the electronics module are securely coupled together.

Furthermore, the main body of the electronics module may also include a temperature sensor, a pivotal position detector, a lighting device and/or at least one status light, as is the case in another preferred embodiment of the invention. In this case the temperature sensor can be configured in such an advantageous way that it extends with its sensor head, parallel to the heating element, through an opening in the rearward wall of the weighing chamber; and its electronic component is positioned inside the main body of the electronics module. As an alternative, it can be provided that a sensor head of the temperature sensor that is less sensitive to automatic flushing processes is arranged inside the chamber that is surrounded by the walls of the weighing chamber, and this sensor head is coupled with an electronic unit in the main body of the electronics module via an electrical contact point in the region of the rearward wall of the weighing chamber.

One aspect underlying these embodiments of the invention is that all of the electronics relating to the heating element are concentrated in the electronics module, in particular, in the main body of the electronics module. In a consistent continuation of this approach, this means that, furthermore, it is preferably provided that the main body of the electronics module comprises an electronic control unit to operate the heating element; and the electronic control unit is in communication with a control unit of the balance, where the control unit is arranged in the base. The result of this arrangement is that the base and the hood are largely independent of each other, thus, largely independent of the balance and the heating device. Both the heating element itself as well as its electronic power unit and the associated electronic control unit are concentrated in the hood, in particular, its electronics module. To the remaining components of the measuring instrument, in particular, to the balance, embodied in the base, only one connection has to exist in order to enable communications at a relatively high level of abstraction. As a result, it is possible to use the same base to manufacture different measuring instruments for different applications, which require different types of heating elements and/or different power outputs of the heating elements. The electronic control unit, which is attached by via a cable or a wireless connection, in the hood only has to receive comparatively simple commands, such as heat output levels and/or target temperatures. The necessary instructions to correctly activate the particular heating element or its electronic power unit are generated by the specialized electronic control unit in the electronics module.

With respect to the ease of cleaning the entire device it is preferably provided that the base surface is configured without a step. In other words, the floor of the weighing chamber forms a flat surface, through which the support of the weighing pan only extends in the vertical direction.

The main body of the electronics module is preferably connected to the base with at least one hook-shaped hinge that surrounds the rearward edge of the base surface. Such a hook-shaped hinge can be fixed or, more specifically, hinged, on the one hand, on the rearward wall of the main body of the electronics module and, on the other hand, on the rearward wall of the housing of the base. The mutually contacting surfaces, i.e., the bottom edges of the walls of the weighing chamber and the floor of the weighing chamber remain unaffected by this and can be configured so as to be flat and easy to clean.

Preferably the at least one hook-shaped hinge is reversibly connected to the main body of the electronics module or the base. For example, a reversible latching mechanism can be provided. This latching mechanism allows the base and the electronics module to be easy decoupled, which is advantageous with respect to the ease, with which the end user can replace the hood.

It is convenient if the surface of the base is formed by a removable cover plate, which rests on a main body of the base and which acts as the floor of the weighing chamber. This means that the actual floor of the weighing chamber is configured as a separate element, which is just as easy to separate from the rest of the measuring instrument and just as easy to clean as the mechanical module; in particular, it can be set into a washing machine.

With respect to cleaning ease, the required opening in the cover plate in the region of the weighing pan support, which passes through the cover plate, is problematic. This opening is preferably formed quite large in order to make it easy to put on and take off this cover plate without any risk of colliding with the support of the weighing pan. On the other hand, a large hole runs the risk that if the sample to be weighed falls off, it may drop under the cover plate and contaminate the underlying parts of the base. In order to prevent this situation from happening, it is provided in a preferred further development of the invention that the cover plate has a recess, through which the weighing pan support passes and in which a sealing sleeve, which is supported on the surface of the cover plate and is secured in a receptacle of the main body of the base, is arranged. This sealing sleeve fulfills three functions. First, it reduces the size of the opening through the cover plate to the minimum amount required for the weighing pan support to move freely. Secondly, it forms with its collar-shaped pad an anti-contamination step; and thirdly, it is used to secure the cover plate, since it is secured with its lower part in the receptacle of the main body of the base and rises with its upper end, like a collar, above the rim of the opening.

In this context it is considered to be particularly convenient, if the sealing sleeve is secured in the receptacle by a screw or bayonet connection; and the height of the sealing sleeve is dimensioned in such a way that this sealing sleeve is under spring bias, which is generated by the elasticity of the diaphragm of the cover plate, in the vertical direction. The bayonet or screw lock has proven to be particularly easy to handle. If the sealing sleeve is dimensioned in its length in such a way that it can be screwed in until its upper collar easily and elastically bends the cover plate downward, then the cover plate acts as a diaphragm spring, which tends to pull the collar upward. This arrangement compensates for any play in this area; and the sealing sleeve is also prevented in a force locking manner from exercising a lateral movement that could lead to an unwanted collision of the sealing sleeve with the support of the weighing pan.

The person skilled in the art will understand that the term "cover plate" in this context is not to be construed as limited to specific materials, in particular, not to metallic materials. Instead, the term "plate" is intended to be understood as a thin, flat unit, which is elastic preferably in the manner of a diaphragm spring and which may also be made, in particular, of a synthetic plastic material.

Additional features and advantages of the invention will become apparent from the following specific description and the drawings.

DETAILED DESCRIPTION

Figure 1:
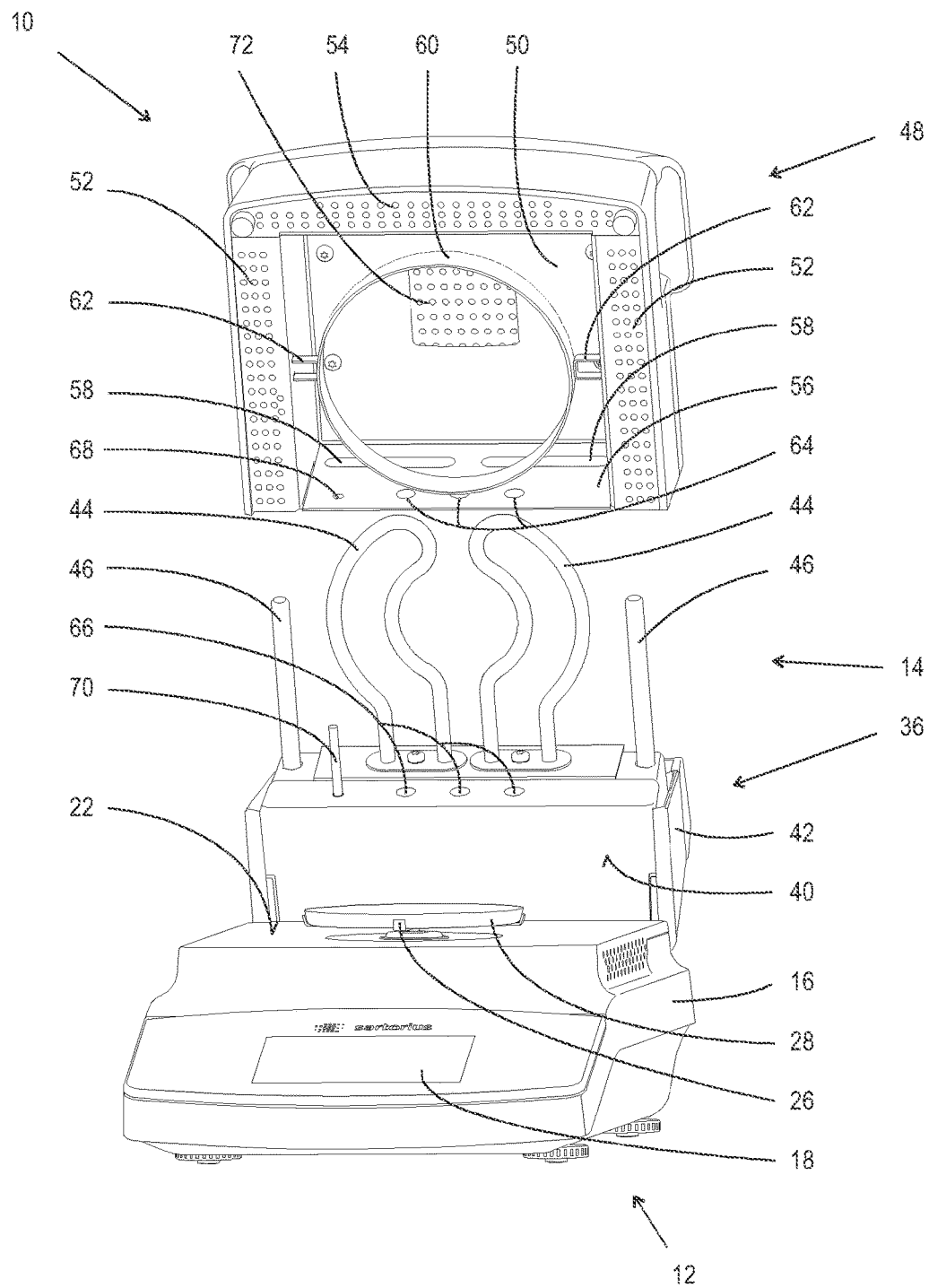
FIG. 1: a perspective view of an inventive measuring instrument with the mechanical module removed.
Figure 2:
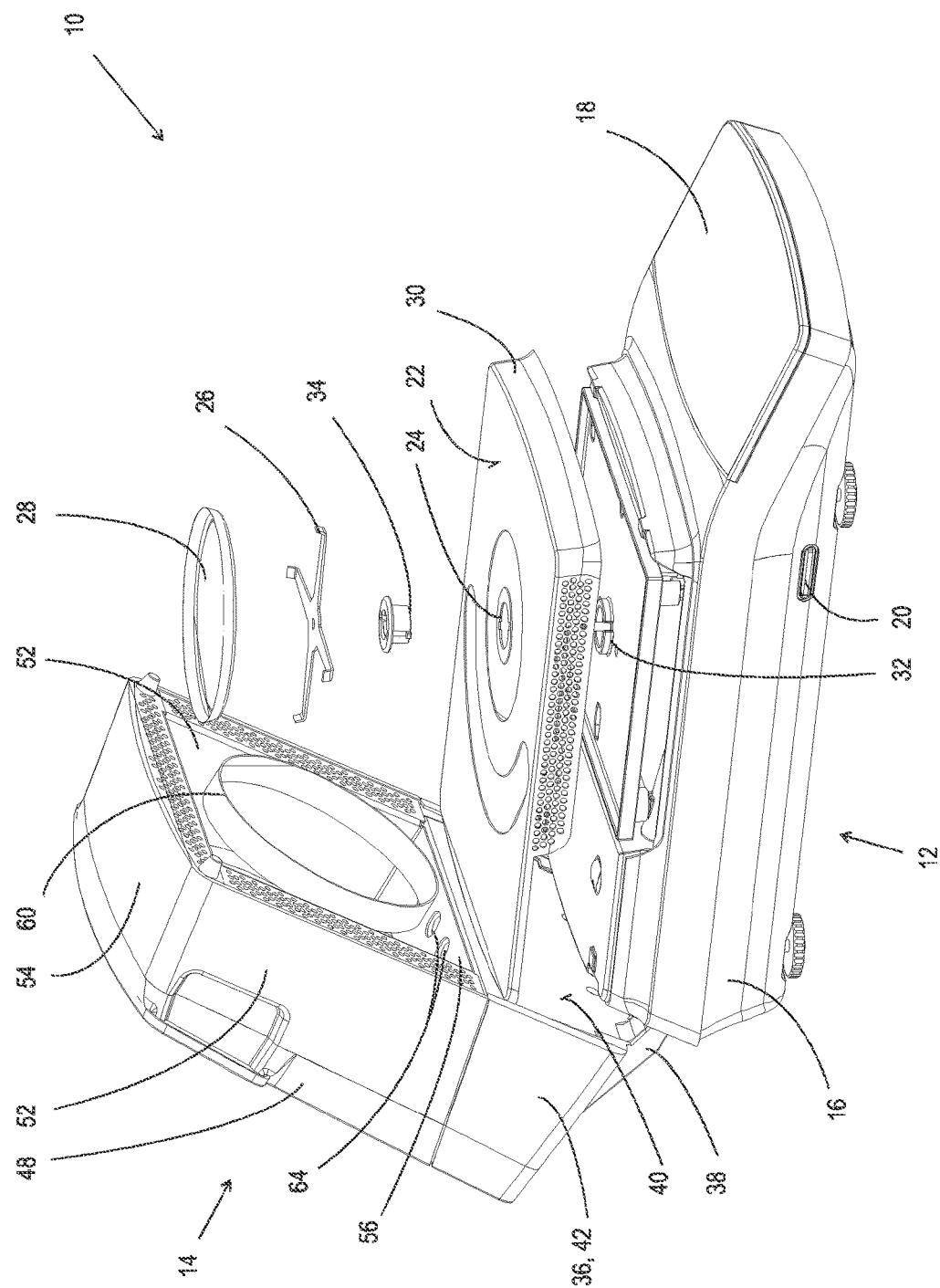
FIG. 2: an exploded view of an inventive measuring instrument with the mechanical module mounted thereon.

Identical reference numerals in the figures refer to the same or analogous elements. FIGS. 1 and 2 show an embodiment of an inventive measuring instrument 10 for thermogravimetrically determining the moisture content of a material in different views and representations and will be discussed together below.

The measuring instrument 10 consists in essence of two components, i.e., a base 12 and a hood 14 that is pivotally hinged to the base 12. The base 12 is configured as a balance with a housing 16 that contains a weighing device (not shown in more detail), in particular, a weighing device that works on the principle of electromagnetic compensation. Furthermore, an electronic control unit (not shown in more detail) for actuating the weighing device is placed in the housing. In the front area of the housing 16 there is a user interface 18 that is designed as a display. In a lateral region of the housing 16 there is also an electrical interface 20. The surface 22 of the housing 16 is configured as a step-free plane that has a central opening 24, which in the final assembled state is vertically traversed by a vertical arm (not shown in more detail in the figures) of a weighing pan support. A cross arm 26 of the weighing pan support is positioned on the vertical arm of the weighing pan support; and a weighing pan 28 for receiving the sample (not shown) to be weighed can be placed on the cross arm. The weight of a sample that is to be weighed and that is placed on the weighing pan 28 acts via the weighing pan support on the load arm (not shown) of the weighing device, which in interaction with its electronic control unit can measure the weight of the sample to be weighed or, more specifically, the weight profile thereof and can bring this weight or rather the weight profile to the attention of a user in a suitable manner.

In the particularly advantageous embodiment of the invention shown in the figures, the surface 22 is formed as a thin-walled cover plate 30, which is arranged, as can be seen especially in FIG. 2, on the housing 16 in such a way that the cover plate can be removed. Below the cover plate 30 there is a bayonet sleeve 32, which surrounds the vertical arm of the weighing pan support. A sealing ring 34 with a corresponding bayonet insert is guided through the opening 24 in the cover plate 30, where in this case the sealing ring has an annular collar that rests on the rim of the opening 24. After having introduced the sealing ring 34 into the bayonet sleeve 32, both elements can be locked to each other by rotating the sealing ring 34; and, in so doing, the sealing ring 34 is pulled so far into the bayonet sleeve 32 that its collar pulls the rim of the opening 24 slightly downwards, so that the sealing ring 34 is under vertically directed diaphragm tension of the cover plate 30. On the one hand, this arrangement will provide that the sealing ring 34 is secure against any undesired play; and, on the other hand, the cover plate 30 will be simultaneously securely fixed on the housing 16.

The hood 14 consists of two modules that can be separated from each other, as can be seen especially in FIG. 1. An electronics module 36 is pivotally hinged via hook-shaped hinges 38 to the rearward wall of the base 12. In this context the hinging can be done in such a way that in the closed state the hood 14 can rest with the bottom side in subareas on the surface 22 of the base 12, i.e., on one area of the cover plate 30. The main body 42 contains in its interior an electronic power unit for two heating elements 44 and, in addition, preferably contains an electronic control unit for the heating elements or, more specifically, for their electronic power unit. The heating elements 44 themselves are not integrated into the main body 42. Instead, they protrude from the end face thereof. Laterally of the heating elements there are guide rods 46 that extend out, parallel to the heating elements 44, from the main body 42.

The second module of the hood 14, which is referred to herein as the mechanical module 48, comprises in essence a weighing chamber lid 50, two side walls 52 of the weighing chamber, a front wall 54 of the weighing chamber and a rearward wall 56 of the weighing chamber, all of which together form a downwards open chamber that is otherwise more or less closed. In the closed state of the hood 14 the lid 50 and the walls 52, 54, 56 form, together with the surface 22 of the base 12, a weighing chamber that encloses the weighing pan 52.

In the rearward wall 56 of the weighing chamber there are slot-like openings 58 that are dimensioned in such a way that when the mechanical module 48 is slid linearly onto the guide rods 46, the heating elements 44 pass through the opening and extend into the weighing chamber. For this purpose the side walls 52 of the mechanical module 48 are equipped with guide channels (not shown) that are dimensioned to correspond to the guide rods 46. FIG. 1 shows the inventive measuring instrument with the mechanical module removed; and FIG. 2 shows this measuring instrument with the mechanical module 48 mounted thereon.

In the interior of the chamber surrounded by the walls 52, 54, 56, there is an annular draft shield 60 that is secured on the side walls 52 with webs 62 in the embodiment shown. The draft shield 60 is dimensioned and arranged in such a way that it surrounds the weighing pan 28 like a ring when the hood 14 is in the closed state.

In addition, the rearward wall 56 of the mechanical module 48 has additional openings 64, through which light can enter from a lighting element 66 that is arranged on the end face of the main body 42. In the final assembled state a temperature sensor 70 can pass through another opening 68 of the rearward wall 56 of the mechanical module 48. In this case the temperature sensor protrudes, parallel to the guide rods 46, from the end face of the main body 42. When the system is running, this temperature sensor can be used to measure the temperature in the weighing chamber.

Finally the weighing chamber lid 50 of the mechanical module 48 is provided with an inspection window 72, through which the procedures in the weighing chamber can be observed when the system is running. In the mounted state the mechanical module 48 can be secured on the main body 42, preferably with a latching device, which is not shown in detail.

The embodiments, discussed in the specific description and shown in the figures, are illustrative, exemplary embodiments of the present invention. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

LIST OF REFERENCE NUMERALS 10 measuring instrument
12 base
14 hood
16 housing
18 user interface
20 electrical interface
22 surface of 12
24 recess in 22
26 cross arm of the weighing pan support
28 weighing pan
30 cover plate
32 bayonet sleeve
34 sealing ring
36 electronics module
38 hook-shaped hinge
40 bottom side of 42
42 main body of 36
44 heating element
46 guide rod
48 mechanical module
50 weighing chamber lid
52 side wall of the weighing chamber
54 front wall of the weighing chamber
56 rearward wall of the weighing chamber
58 opening in 56
60 draft shield
62 web
64 opening in 56
66 lighting element
68 opening in 56
70 temperature sensor
72 inspection window

What is claimed is:

1. A measuring instrument for thermogravimetrically determining a moisture content of a material, comprising
a base, which is configured as a balance and which has a base surface, which forms at least one weighing chamber floor and through which a weighing pan support passes, and
a hood, which is pivotably connected to the base and which forms a weighing chamber lid and a plurality of weighing chamber walls including a rearward weighing chamber wall, as well as at least one heating element, configured to heat the chamber that is formed by the weighing chamber lid and the weighing chamber walls and which is in electrical contact with an electronic power unit,
wherein the hood comprises an electronics module comprising the heating element and the electronic power unit, and a mechanical module comprising the weighing chamber lid and the plurality of weighing chamber walls, and
wherein the mechanical module is rigidly and reversibly coupled to the electronics module such that the heating element, which protrudes from a main body of the electronics module, extends through a corresponding opening in the rearward weighing chamber wall, and the main body is pivotably connected to the base and surrounds the electronic power unit.

2. The measuring instrument as claimed in claim 1, wherein
in parallel with the heating element, at least one guide rail protrudes from the main body of the electronics module, and the mechanical module is mounted reversibly onto the guide rail with corresponding guide elements.

3. The measuring instrument as claimed in claim 1, wherein
the mechanical module has a ring-shaped draft shield, which is arranged in the chamber surrounded by the weighing chamber walls and which in a closed state of the hood surrounds the weighing pan support.

4. The measuring instrument as claimed in claim 1, wherein
the main body of the electronics module comprises a coupling detector configured to detect a current state of coupling between the electronics module and the mechanical module.

5. The measuring instrument as claimed in claim 1, wherein
the main body of the electronics module comprises a temperature sensor, a pivotal position detector, a lighting device and/or at least one status light.

6. The measuring instrument as claimed in claim 1, wherein
the main body of the electronics module comprises an electronic control unit to operate the heating element, the electronic control unit is in communication with a control unit of the balance, and the control unit is arranged in the base.

7. The measuring instrument as claimed in claim 1, wherein
the base surface is formed by a removable cover plate that is configured as an at least substantially flat surface.

8. The measuring instrument as claimed in claim 1, wherein
the main body of the electronics module is connected to the base via at least one hook-shaped hinge surrounding a rearward edge of the base surface.

9. The measuring instrument as claimed in claim 8, wherein
the at least one hook-shaped hinge is reversibly connected to the main body of the electronics module or the base.

10. The measuring instrument as claimed in claim 1, wherein
the base surface is formed by a removable cover plate, which rests on a main body of the base.

11. The measuring instrument as claimed in claim 10, wherein
the cover plate has a recess, through which the weighing pan support passes and in which a sealing sleeve, which is supported on the surface of the cover plate and is secured in a receptacle of the main body of the base, is arranged.

12. The measuring instrument as claimed in claim 11, wherein
the sealing sleeve is secured in the receptacle by a screw or bayonet connection having a height dimensioned to place the connection under a spring bias generated by a diaphragm elasticity of the cover plate and extending in a vertical direction.

13. The measuring instrument as claimed in claim 1, wherein the corresponding opening extends through the rearward weighing chamber wall from the main body to the chamber.

14. The measuring instrument as claimed in claim 1, wherein the heating element is rigidly and reversibly coupled to the main body of the electronics module independent of the rigid and reversible coupling between the mechanical module and the electronics module.

\* \* \* \* \*